United States Patent
Tian et al.

(10) Patent No.: US 7,051,606 B2
(45) Date of Patent: May 30, 2006

(54) DOSAGE FORM HOLDER DEVICE AND METHODS FOR IMMERSION TESTING

(75) Inventors: Dacheng Tian, Miramar, FL (US); Xiu Xiu Cheng, Weston, FL (US); Jack Cardinal, Tamarac, FL (US); Boyong Li, Morgantown, WV (US); Avinash Nangia, Weston, FL (US)

(73) Assignee: Andrx Labs LLC, Davie, FL (US)

( * ) Notice: Subject to any disclaimer, the term of this patent is extended or adjusted under 35 U.S.C. 154(b) by 0 days.

(21) Appl. No.: 10/768,277

(22) Filed: Jan. 30, 2004

(65) Prior Publication Data

US 2005/0166688 A1 Aug. 4, 2005

(51) Int. Cl.
*G01N 33/15* (2006.01)

(52) U.S. Cl. .............. 73/866; 73/864.91; 366/140; 366/244

(58) Field of Classification Search .............. 73/432.1, 73/864.91, 866; 366/140, 241–261; 422/224
See application file for complete search history.

(56) References Cited

U.S. PATENT DOCUMENTS

| | | | |
|---|---|---|---|
| 3,572,648 A | 3/1971 | Hanson | |
| 3,614,434 A | 10/1971 | Horwitz et al. | |
| 3,742,190 A | 6/1973 | Giani et al. | |
| 3,791,221 A * | 2/1974 | Kirschner et al. | 73/866 |
| 3,791,222 A * | 2/1974 | Goodhart et al. | 73/866 |
| 3,802,272 A * | 4/1974 | Bischoff et al. | 73/866 |
| 4,669,771 A | 6/1987 | Finneran | |
| 4,754,657 A * | 7/1988 | Schneider | 73/866 |
| 4,856,909 A | 8/1989 | Mehta et al. | |
| 4,879,917 A * | 11/1989 | Eppelmann et al. | 73/866 |
| 5,076,107 A * | 12/1991 | Timmermans et al. | 73/866 |
| 5,142,920 A | 9/1992 | Bart et al. | |
| 5,178,867 A * | 1/1993 | Guittard et al. | 424/473 |
| 5,412,979 A | 5/1995 | Fassihi | |
| 5,589,649 A | 12/1996 | Brinker et al. | |
| 5,816,701 A | 10/1998 | Martin et al. | |
| 5,827,984 A * | 10/1998 | Sinnreich et al. | 73/866 |
| 6,170,980 B1 | 1/2001 | Martin | |
| 6,174,497 B1 * | 1/2001 | Roinestad et al. | 422/82.05 |
| 6,303,909 B1 * | 10/2001 | Fernando et al. | 219/429 |
| 6,336,739 B1 * | 1/2002 | Lee | 366/143 |
| 6,419,954 B1 * | 7/2002 | Chu et al. | 424/465 |
| 6,497,157 B1 * | 12/2002 | Viegas et al. | 73/866 |
| 2003/0180360 A1 * | 9/2003 | Am Ende et al. | 424/468 |
| 2005/0048119 A1 * | 3/2005 | Nangia et al. | 424/473 |

OTHER PUBLICATIONS

Soltero et al., "Effects of Sinker Shapes on Dissolution Testing", Jan. 1989, Journal of Pharmaceutical Sciences, vol. 78, No.1, pp. 35-39.*

(Continued)

*Primary Examiner*—Hezron Williams
*Assistant Examiner*—David A. Rogers
(74) *Attorney, Agent, or Firm*—Hedman & Costigan, P.C.; James V. Costigan, Esq.; Martin P. Endres, Esq.

(57) ABSTRACT

The present invention comprises a device and methods for dissolution or immersion testing and, in particular, a device and methods that improve the consistency of test results by limiting the ability of pharmaceutical or other dosage forms to move or reorient during testing.

11 Claims, 15 Drawing Sheets

OTHER PUBLICATIONS

Dissolution Testing Product Catalog—Quality Lab Accessories, pp. 1-32.*

Pillay et al., "Unconventional Dissolution Methodologies", Sep. 1999, Journal of Pharmaceutical Sciences, vol. 88, No. 9, pp. 843-851.*

Pillay et al., "Evaluation and Comparison of Dissolution Data Derived from Different Modified Release Dosage Forms: An Alternative Method", 1998, Journal of Controlled Release, vol. 55, pp. 45-55.*

"Acceptance of Sinker Baskets", available on the Internet at <http://www.dissolution.com>.*

"Stagnant Areas—High Variability", available on the Internet at <http://www.dissolution.com>.*

Wu et al., "Effect of Fill Weight, Capsule Shell, and Sinker Design on the Dissolution Behavior of Capsule Formulations of a Weak Acid Drug Candidate BMS-309403", 2003, Pharmaceutical Development and Technology, vol. 8, No. 4, pp. 379-383.*

*Pharmaceutical Technology*, Oct. 23, 2003, Study Highlights Flawed Testing Procedure.

*U.S. Pharmacopeia*, 2002, 25, pp. 2010-2012.

www.tabletdissolution.com.

* cited by examiner

DOSAGE FORM HOLDER DEVICE AND METHODS FOR IMMERSION TESTING

FIELD OF INVENTION

The present invention relates to a device and methods for testing pharmaceutical dosage forms such as tablets or capsules. More particularly, the present invention relates to a device and methods for dissolution or immersion testing that limit the ability of a tablet or capsule to move or reorient during testing. Most particularly, the present invention relates to a device and methods that provide for more consistent and/or accurate results in dissolution or immersion testing of tablets or capsules.

BACKGROUND OF THE INVENTION

In pharmaceutical and laboratory research and development, it is commonplace, during formulation development, stability determination, analytical method development, quality control, or otherwise, to ascertain the rate at which a solid dissolves under certain well-defined conditions and/or to predict how it will dissolve in the human system. By way of example, detailed procedures for conducting such testing and specifications for the apparatus employed therein are outlined in the publications of the American Pharmaceutical Association's Drug Standards Laboratory, the United States Pharmacopoeia ("USP") and the National Formulary. By way of further example, USP 25 <711> Dissolution, which is incorporated herein by reference, describes a test to determine compliance with the dissolution requirements that are stated in the individual monograph for a particular drug. The current USP specifies two alternative apparatuses to be used for the test.

Apparatus 1 (or type 1 apparatus) consists of a vessel made of glass or other inert transparent materials with one of the following dimensions and capacities: for a nominal capacity of 1 liter, the height is 160 mm to 210 mm and its inside diameter is 98 mm to 106 mm; for a nominal capacity of 2 liters, the height is 280 mm to 300 mm and its inside diameter is 98 mm to 106 mm; and for a nominal capacity of 4 liters, the height is 280 mm to 300 mm and its inside diameter is 145 mm to 155 mm. Its sides are flanged at the top. The apparatus further consists of a motor, a metallic drive shaft and a cylindrical basket. See FIG. 17. It is specified that the shaft and basket components of the stirring element are fabricated of stainless steel, type 316 or equivalent, to the specifications shown in FIG. 1 of the USP. It is further specified that the basket may be coated with a thin layer of gold.

Apparatus 2 (or type 2 apparatus) is essentially the same as apparatus 1 except that a paddle formed from a blade and a shaft is used as the stirring element rather than a basket. See FIG. 18. USP specifies as follows: the paddle conforms to the specifications shown in FIG. 2 thereof; the distance of 25±2 mm between the blade and the inside bottom of the vessel is maintained during the test; the metallic or suitably inert, rigid blade and shaft comprise a single entity; a suitable two-part detachable design may be used provided the assembly remains firmly engaged during the test; and the paddle blade and shaft may be coated with a suitable inert coating.

In testing, the dosage form is allowed to sink to the bottom of the vessel before rotation of the paddle is started. The USP further provides that a small, loose piece of non-reactive material such as a few turns of wire may be attached to dosage forms that would otherwise float and that other validated sinker devices may be used. Such devices may be formed of a material that is not easily corrodible by the dissolution medium, which may be acidic.

The testing procedure provided for in USP 25 <711> Dissolution is generally as follows. The stated volume of dissolution medium is placed in the vessel specified in the individual monograph for the drug being tested, the apparatus is assembled, and the medium is temperature equilibrated to 37° C.±0.5° C. (to approximate in vivo conditions). Thereafter, the dosage form is placed in the apparatus and the apparatus is operated at the rate specified in the individual monograph. Within the time interval specified, or at each of the stated times, a specimen is withdrawn from the vessel. Often the test is repeated in different vessels and/or with a second, third, or additional dosage form of the drug being tested.

Hence, it is known in the art to entrap dosage forms in a gold coated and/or stainless steel wire basket or in a few turns of non-corrosive wire. In addition, there are commercially available sinkers designed to hold a gelatin capsule in place in a USP 25 <711> Dissolution type 2 apparatus until it dissolves. Examples of commercially available capsule sinkers may be found at www.tabletdissolution.com. However, such devices are not designed to hold a tablet in a specific orientation during testing or to be used in conjunction with conventional dissolution baskets.

It is also known in the art to limit capsule movement during testing. Apparatus 7 of USP 25 <724> Drug Release teaches a holder designed for coated oral extended release tablets. See FIG. 19. Apparatus 7 specifies the use of a vertically reciprocating spring holder attached to a stainless steel tube and Sample Preparation A, USP 25 <724> Drug Release, allows for the use of a small nylon net bag at the end of a plastic rod. Such holders, however, have drawbacks. For example, the adhesive used to attach the tablets to the rod of the holder can compromise test results by affecting the rate-controlling coating and, thereby, the drug release profile. Additionally, such holders are not useful for tablets with a thin coating or shell because the coating or shell is likely to collapse and dump its content due to the upward and downward strokes of the holder during testing.

Finneran, U.S. Pat. No. 4,669,771, teaches a device for loosely holding a capsule during fluid immersion testing with a plurality of gripping fingers connected at one end which fingers surround a chamber to receive and retain a capsule. However, the device is not suitable for immersion testing of tablets. Fassihi, U.S. Pat. No. 5,412,979, teaches a disk that restrains a dosage form from floating to top of a fluid medium during testing using a vertical shaft and blade apparatus. However, the device is not designed to hold a dosage form in a specific orientation during testing or to be used in conjunction with a dissolution basket. In addition, it is known that differences in hydrodynamic effects corresponding to the relative position of test tablets in test vessels are likely to cause high variability in dissolution testing. See Study Highlights Flawed Dissolution Testing Procedure, *Pharmaceutical Technology*, October 2003, at 18–19.

The present invention provides a device and methods for immersion and dissolution testing whereby a tablet (by way of example, a controlled release tablet such as an osmotic tablet or matrix tablet) or capsule is held in a specific orientation or substantially fixed position during testing, which can advantageously provide test results that are more consistent between the different tablets (or capsules) and/or vessels used for the testing. For example, when a tablet begins to dissolve, the change in mass can result in a change in the orientation of the tablet either on the bottom of a dissolution vessel, or within a basket, if the movement of the tablet is not limited. A change in orientation of the tablet can result in variability of dissolution characteristics between different tablets of the particular drug being tested and/or vessels used for the testing.

The inventors have found the present invention is also well suited for use with tablets having a preformed passageway, e.g., laser drilled, such as an osmotic tablet with a semi-permeable membrane surrounding the tablet. If a tablet with a preformed passageway(s) reorients during dissolution testing, the test results may be altered if the reorientation interferes with diffusion of the medicament from the passageway(s). For example, if the tablet orients so that the passageway exit is at its bottom, the dissolved contents tend to "dump" out of the exit faster than if the exit is maintained at the top or side of the tablet. By maintaining the exit on the sides (if two exits) and/or on the side or top (if one exit), the contents are prevented from dumping, which allows a steadier rate of diffusion of the contents, including the active drug.

In addition, with respect to controlled-release dosage form tablets such as matrix tablets, the mass of the dosage form diminishes over time. Maintaining the orientation of such a tablet provides for a greater precision in results between different tablets of the particular drug being tested and/or vessels used for the testing.

The subject invention can also prevent tablets or capsules and their contents from sticking to the testing vessel. For example, as tablets dissolve, certain excipients, which may have adherent properties, can cause a tablet to adhere to the inner surface of the vessel. There is a high degree of variability in tablets that adhere to the vessel, which can also cause variability in dissolution between different tablets or capsules of the particular drug being tested and/or vessels used for the testing. By preventing such dosage form adhesion, the subject invention also can provide test results that are more accurate and/or consistent. The subject invention limits variability of location and orientation of tablets and capsules during dissolution testing, which also limits variation from vessel to vessel during testing.

SUMMARY OF THE INVENTION

The present invention comprises a device and methods that provide for more consistent and/or accurate dissolution or immersion test results.

Thus, it is an object of the present invention to provide a useful device that can limit the movement of a dosage form, preferably a tablet, during testing in an immersion or dissolution apparatus.

It is another object of the present invention to provide a useful device that can prevent dosage forms such as tablets or capsules from floating in, or adhering to, testing vessels.

It is still another object of the present invention to provide a useful device that may be used in conjunction with conventional dissolution apparatus without requiring modification of the equipment.

It is a further object of the present invention to provide methods of improving the consistency of dissolution or immersion testing results.

In apparatus terms, these and other objectives are achieved by a device for holding dosage forms such as tablets or capsules during immersion testing comprising: an enclosure surrounding a chamber sufficiently large to receive a dosage form therein; a retaining means; wherein said retaining means engages with said enclosure to limit the movement of a dosage form within said chamber.

In method terms, these and other objectives are achieved by the present invention that provides methods for performing immersion testing comprising the steps of: placing a dosage form, preferably a tablet, into a device for holding the dosage form in a specific orientation, placing said device in immersion testing apparatus and conducting immersion testing.

DETAILED DESCRIPTION OF THE INVENTION

Figure 1:
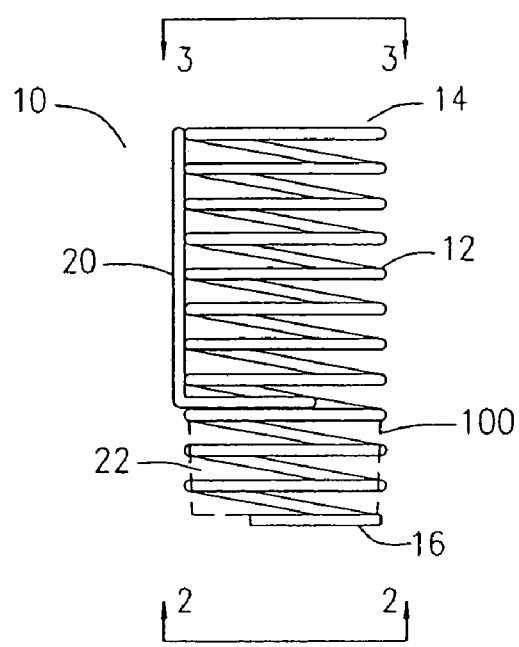
FIG. 1 depicts a perspective view of one embodiment of the bolder of the present invention.

Referring to FIG. 1, there is shown a dosage form holder 10 of the present invention. In the depicted embodiment, the holder is comprised of an enclosure 12, in this case a cylindrical coil, with a first end 14 and a second end 16, a support member 18 (shown in FIG. 2), and a retaining means 20. The coil enclosure 12 defines a chamber 22 of a sufficient size to accommodate dosage forms of various shapes and dimensions. As explained below, in operation, the retaining means 20 engages with the enclosure 12 to retain a dosage form 100 in a desired position within the chamber 22. The position of the retaining means with respect to the enclosure may be varied depending on the shape and dimensions of the dosage form to be enclosed.

Figure 2:
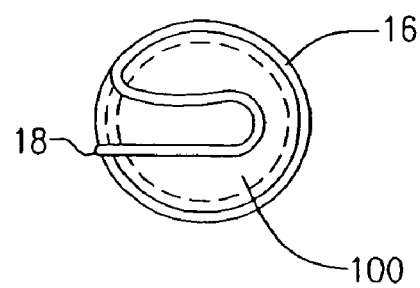
FIG. 2 depicts a view taken along line 2—2 of FIG. 1.
Figure 3:
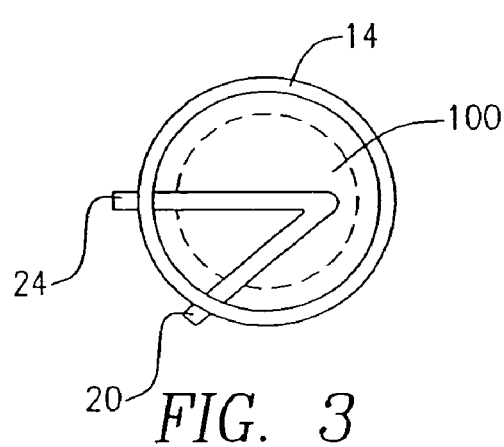
FIG. 3 depicts a view taken along line 3—3 of FIG. 1.

FIG. 2 depicts a view taken along line 2—2 of FIG. 1. The second end 16 of the coil enclosure 12 has a support member 18 upon which a dosage form such as a tablet 100 may rest. FIG. 3 depicts a view taken along line 3—3 of FIG. 1 showing the end 24 of the retaining means opposite the holding portion 26 (shown in FIG. 4).

Although the embodiments depicted show the enclosure 12 as having a flat first end 14, second end 16 and support member 18, in other embodiments, either or both ends of the enclosure and/or the support member may be rounded rather than flat in order to conform to the shape of the receptacle into which the holder is to be placed. Further, either or both ends of the enclosure and/or the support member may be of any other suitable shape known to those skilled in the art.

Figure 4:
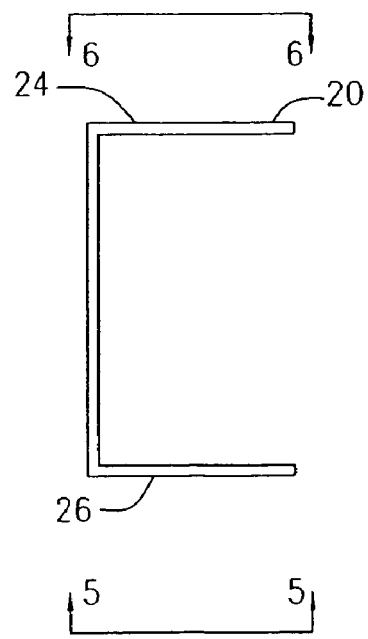
FIG. 4 depicts a perspective view of an embodiment of the retaining means of the present invention.
Figure 5:
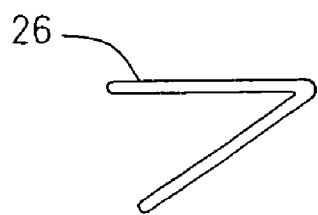
FIG. 5 depicts a view taken along line 5—5 of FIG. 4.

In the embodiment depicted in FIG. 1, the retaining means 20 is independent of the coil enclosure 12. By independent, it is meant that the retaining means is a separate structure from the enclosure. However, in other embodiments, the retaining means may be integrally formed with the enclosure. In still further embodiments, the retaining means may be otherwise attached to the enclosure by any means known to those skilled in the art including, but not limited to, a hinged means. FIG. 4 depicts a retaining means that is independent of the enclosure. FIG. 4 depicts a retaining means 20 that engages with the coil enclosure 12 (not shown) comprising a holding portion 26 that retains a tablet within the chamber 22 (not shown) and an opposite end 24. FIG. 5 depicts a view taken along line 5—5 of FIG. 4 showing the holding portion 26 of the retaining means. In the depicted embodiment, the opposite end of the retaining means (line 6—6 of FIG. 4) is of the same shape as the holding portion. However, in other embodiments, the holding portion 26 and/or the opposite end 24 of the retaining means may take any suitable shape known to those skilled in the art.

Figure 6:
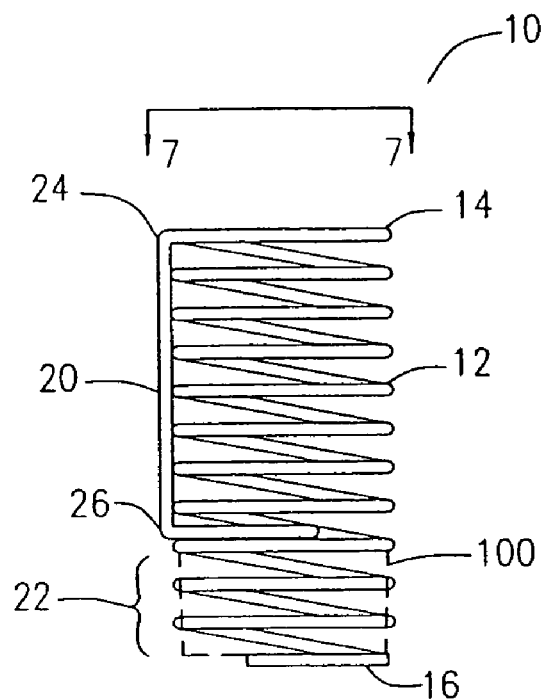
FIG. 6 depicts a perspective view of an embodiment of the holder using another embodiment of the retaining means.
Figure 7:
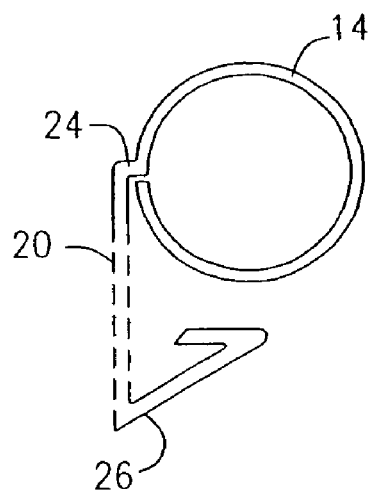
FIG. 7 depicts a view taken along line 7—7 of FIG. 6.

FIG. 6 and FIG. 7 depict an example of a retaining means integrally formed with the enclosure. FIG. 6 depicts a perspective view of one embodiment of the present invention showing a coil enclosure 12 with a first end 14, a second end 16 and a retaining means 20. Also shown is the holding portion 26 of the retaining means 20 and the opposite end 24 of the retaining means that is integrally attached to the first end 14 of the coil enclosure 12. FIG. 7 depicts a view taken along line 7—7 of FIG. 6 showing a retaining means 20 and its holding portion 26 integrally attached at the opposite end 24 to the enclosure, in this case the first end 14 thereof. The operation of such a retaining means is explained below.

Figure 8:
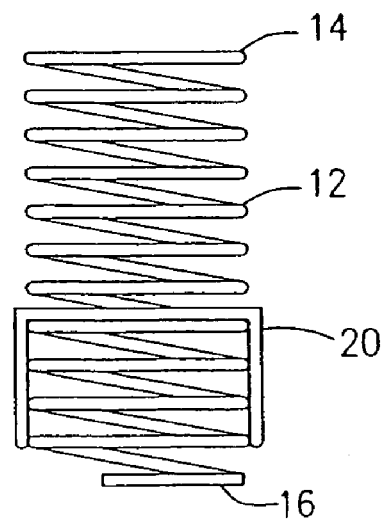
FIG. 8 depicts a perspective view of an embodiment of the holder using yet another embodiment of the retaining means.

FIG. 8 depicts another embodiment of a retaining means 20. Therein is shown a bracket-shaped retaining means 20 that engages with the coil 12, basket or other enclosure. As explained below, in operating the device, the retaining means 20 can be variously positioned between the first end 14 and second end 16 of the enclosure, depending on the dimensions and/or shape of the dosage form and/or the desired positioning of the dosage form.

Although the figures depict circular coils used to define a chamber for enclosing a dosage form in a desired position, other kinds of enclosures are also within the full-intended scope of the present invention. By way of example, but not limitation, a coil of a rectangular, square or of any other suitable shape known to those skilled in the art may be employed. Further, a mesh or woven basket of a circular, cubical, rectangular or any other suitable shape known to those skilled in the art may be employed.

Figure 9:
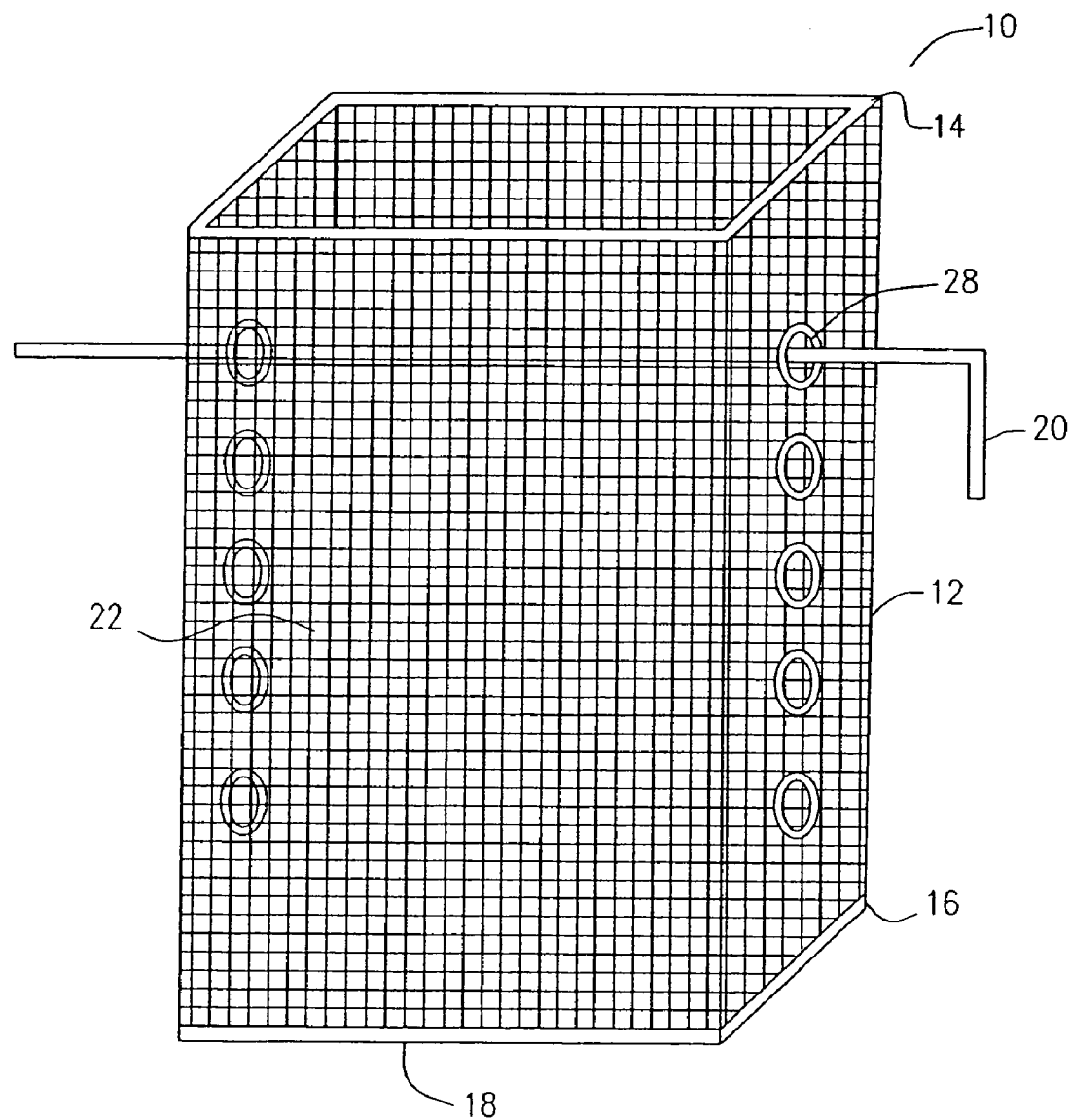
FIG. 9 depicts a perspective view of another embodiment of the holder of the present invention.
Figure 9A:
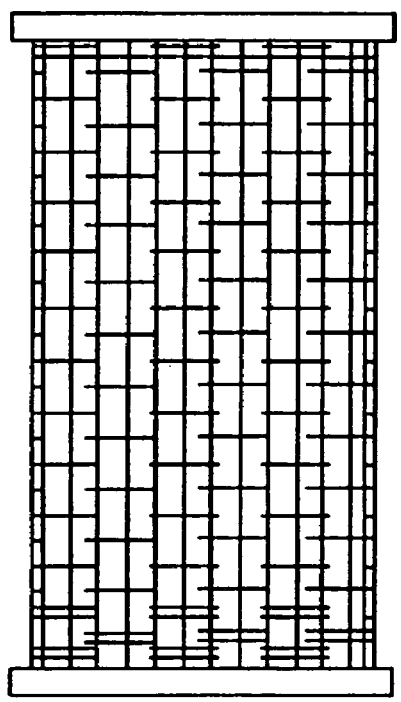
FIG. 9A depicts an alternative embodiment of the present invention.
Figure 9B:
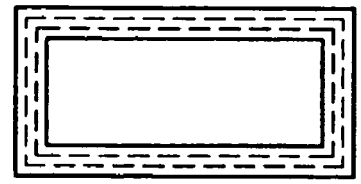
FIG. 9B depicts a top view of the embodiment depicted in FIG. 9A.
Figure 9C:
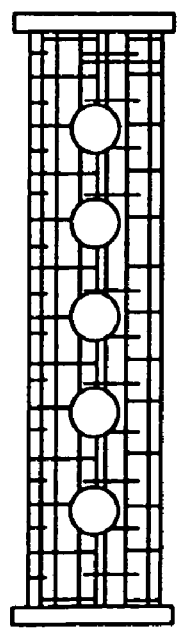
FIG. 9C depicts a side view of the embodiment depicted in FIG. 9A.

FIG. 9 depicts another embodiment of the holder 10 of the present invention comprised of an enclosure 12, in this case a rectangular basket, with a first end 14 and a second end 16, a support member 18 and a retaining means 20. The enclosure 12 defines a chamber 22 of a sufficient size to accommodate tablets or capsules of various shapes and dimensions. As explained below, in operation, the retaining means 20 engages with the enclosure 12 to retain a dosage form 100 (not shown in FIG. 9) in a desired position within the chamber 22. The position of the retaining means with respect to the enclosure may be varied depending on the shape and dimensions of the dosage form to be enclosed. In the depicted embodiment, a plurality of apertures or holes 28 in the enclosure allow for varying the position of the retaining means 20. In this embodiment, the retaining means is independent of the enclosure, i.e., a separate structure forms the enclosure. However, in other embodiments, the retaining means may be integrally formed with the enclosure. Also, the depicted enclosure shows a basket of symmetrical mesh. Alternative embodiments may use asymmetrical or other patterned mesh to form the basket as shown in FIG. 9A. FIGS. 9B and 9C show a top and side view, respectively, of the embodiment depicted in FIG. 9A.

Figure 10:
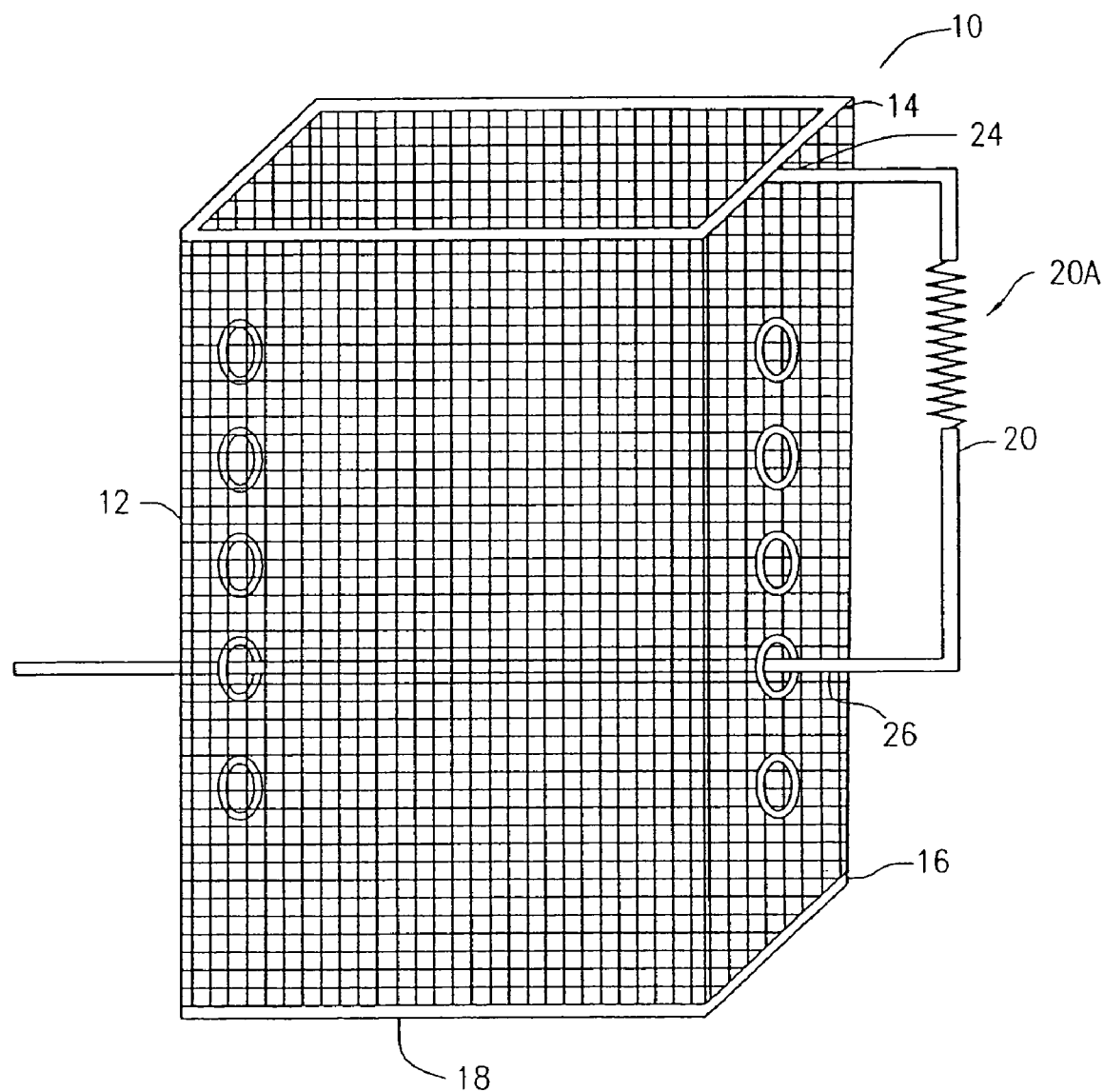
FIG. 10 depicts a perspective view of an embodiment of the holder using another embodiment of the retaining means.

FIG. 10 depicts an example of an embodiment of a holder 10 with a retaining means 20 integrally formed with the enclosure 12. Also shown is the holding portion 26 of the retaining means 20 and the opposite end 24 of the retaining means that is integrally attached to the first end 14 of the enclosure 12. The retaining means 20 may be made of flexible material such as wire or plastic or any other suitable material known to those skilled in the art or may contain a resilient portion 20A that allows the retaining means 20 or, specifically, the holding portion 26, to be moved in a manner that allows positioning of the dosage form in the holder 10. By way of example, the retaining means may be spring loaded so that it can be stretched to position different size dosage forms within the holder 10. The operation of such the retaining means of the invention is further explained below.

Figure 10A:
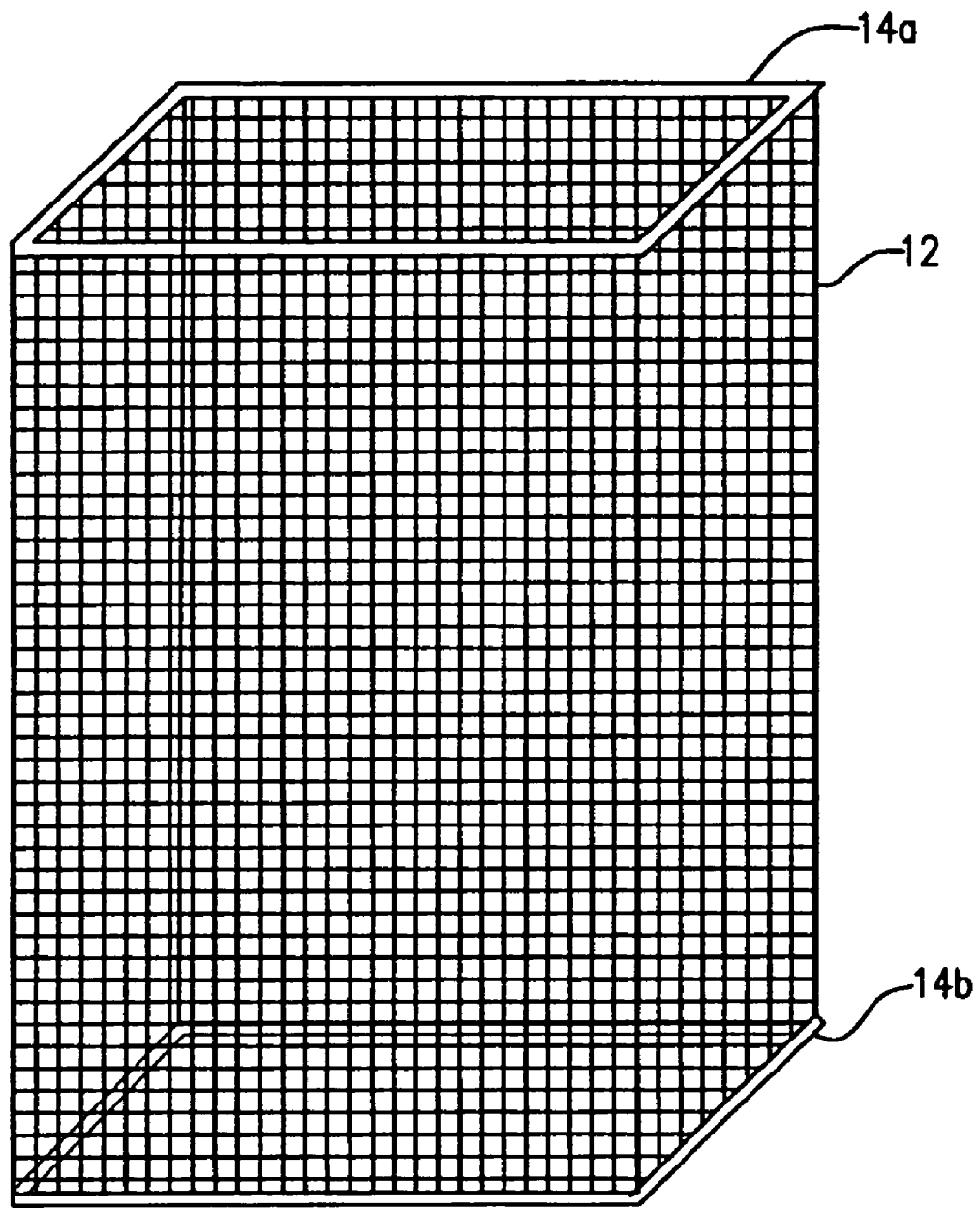
FIG. 10A depicts an embodiment wherein the enclosure is rectangular.

FIG. 10A shows an embodiment wherein the enclosure 12 is made of mesh wire screen, which is shaped into a rectangle with a joint soldered. The two ends of the holder have supports 14*a* and 14*b* that may support the holder. The supports may be made of stainless steel or any suitable material known to those skilled in the art.

In operation of one embodiment of the device, the dosage form such as a tablet 100 may be inserted into the chamber 22 so as to rest on the support member 18 of the enclosure 12. After the dosage form is inserted into the chamber 22, the retaining means 20 may be engaged with the enclosure 12 such that the holding portion 26 thereof prevents passage of a captive dosage form 100 out of chamber 22 and so as to retain loosely (or in any manner desired) the dosage form in a horizontal, vertical or other desired position.

In embodiments where the retaining means is integrally formed with the enclosure, the holding portion of the retaining means may, if necessary, be removed from the chamber within the enclosure prior to insertion of the dosage form. Once the dosage form is inserted into the chamber, the retaining means is bent or otherwise engaged with the enclosure such that its holding portion prevents passage of a captive dosage form out of the chamber and limits the movement of the dosage form. In method terms, once the dosage form, preferably a tablet, is oriented in a desired position within the enclosure, the remaining steps for dissolution or immersion testing may be conducted as desired.

The components of the holder are preferably fabricated of stainless steel, plastic or other material (or any combination thereof) that is not easily corrodible by the dissolution medium, which may be acidic. In the case of a coil enclosure or the like, the material of the coil may also be chosen to provide enough resilience to permit it to be easily collapsed to allow the retaining means to engage greater or fewer rings of the enclosure so as to allow a more precise fit with the retaining means and to adjust to the shape and/or dimensions of the dosage forms being tested. In embodiments where the retaining means is integrally or otherwise attached to the enclosure, the retaining means may be constructed such that it may be moved in and out of position and able to withstand repeated use.

Because the specific gravity of the dosage form may be less than the specific gravity of the immersion medium (which would allow the dosage form to float in the immersion medium), the holder may also serve as a sinker. Where such is the case, the components of the holder can be constructed of materials such that the overall device will have a density greater than that of the dissolution medium(s) used. Other means to keep the holder submersed in the dissolution medium are also within the full-intended scope of the present invention. For example, the device may be submersed by a magnetic means or any other means know to those skilled in the art.

Figure 11:
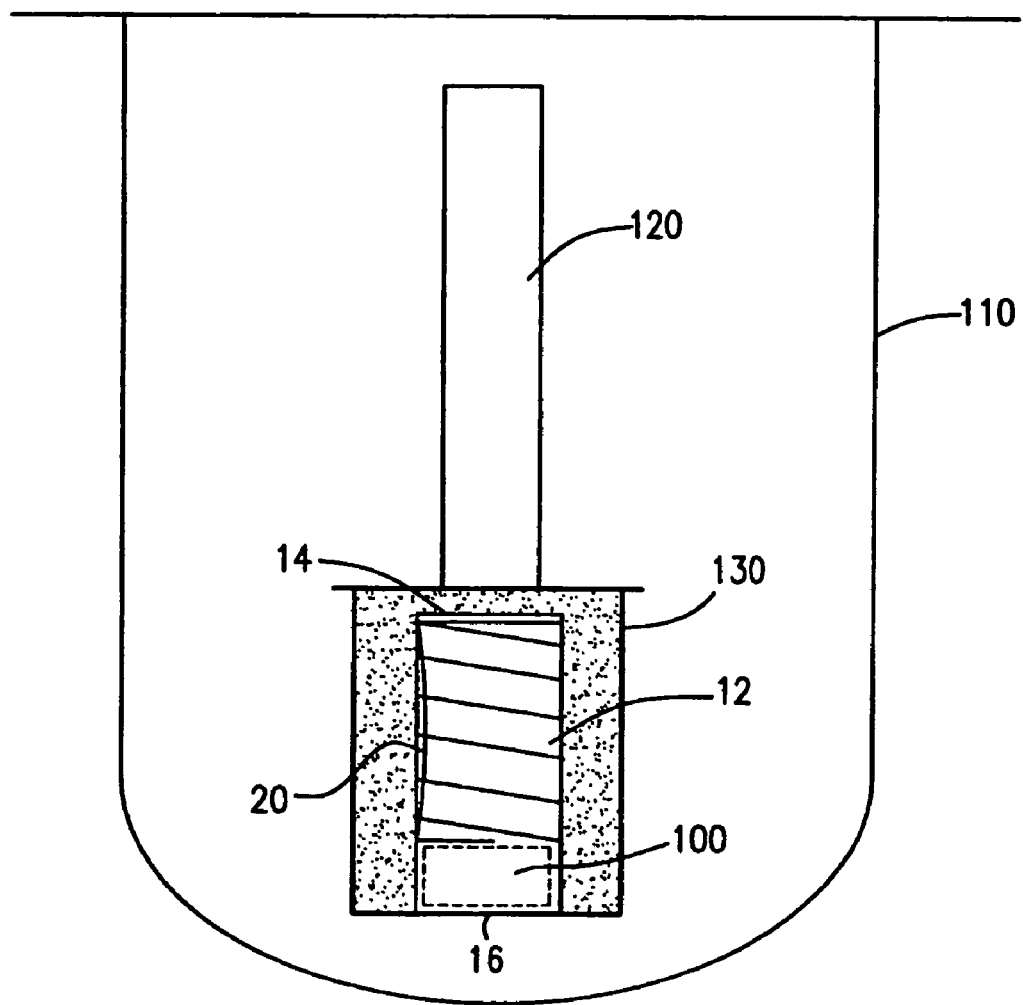
FIG. 11 depicts the embodiment of the present invention shown in FIG. 1 in a USP 25 <711> Dissolution type 1 testing apparatus.
Figure 12:
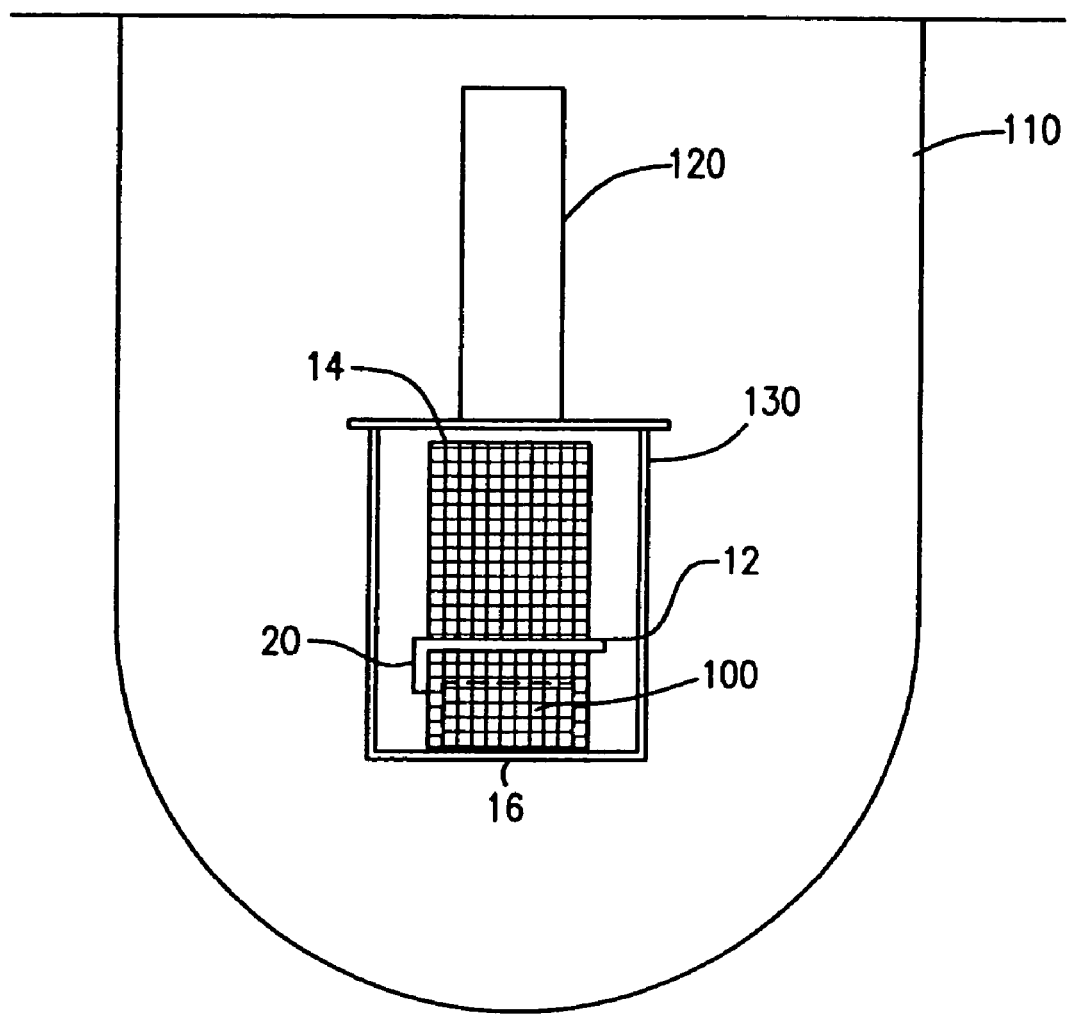
FIG. 12 depicts the embodiment of the present invention shown in FIG. 9 in a USP 25 <711> Dissolution type 1 testing apparatus.

FIG. 11 and FIG. 12 depict a cross-sectional view of the embodiments of the present invention depicted in FIG. 1 and FIG. 9, respectively, used in dissolution apparatus comprised of a vessel 110, shaft 120 and basket 130. The embodiments depicted are of a size and shape such that they nest within a dissolution basket of the dimensions specified in USP 25 <711> Dissolution and/or in a manner that its support member 18 may rest on the bottom of the basket 130 and the enclosure 12 is supported by the inside walls of the basket such that the holder 10 cannot topple over. In addition, the height of the holder 10 depicted is less than the height of the basket 130. Other means of limiting undesired movement of the holder within its receptacle known to those skilled in the art are also within the full-intended scope of the present invention. In addition, it is contemplated that the holder may also be used such that the first end of the enclosure may rest on the bottom of the basket.

As heretofore explained, the present invention may be used with commercially available USP 25 <711> Dissolution type 1 baskets to facilitate the application of the invention without requiring modification to commercially available equipment. In addition, the device may be specially designed to accommodate the shape and dimensions of oversize, undersize or unique sized dosage forms.

Figure 13:
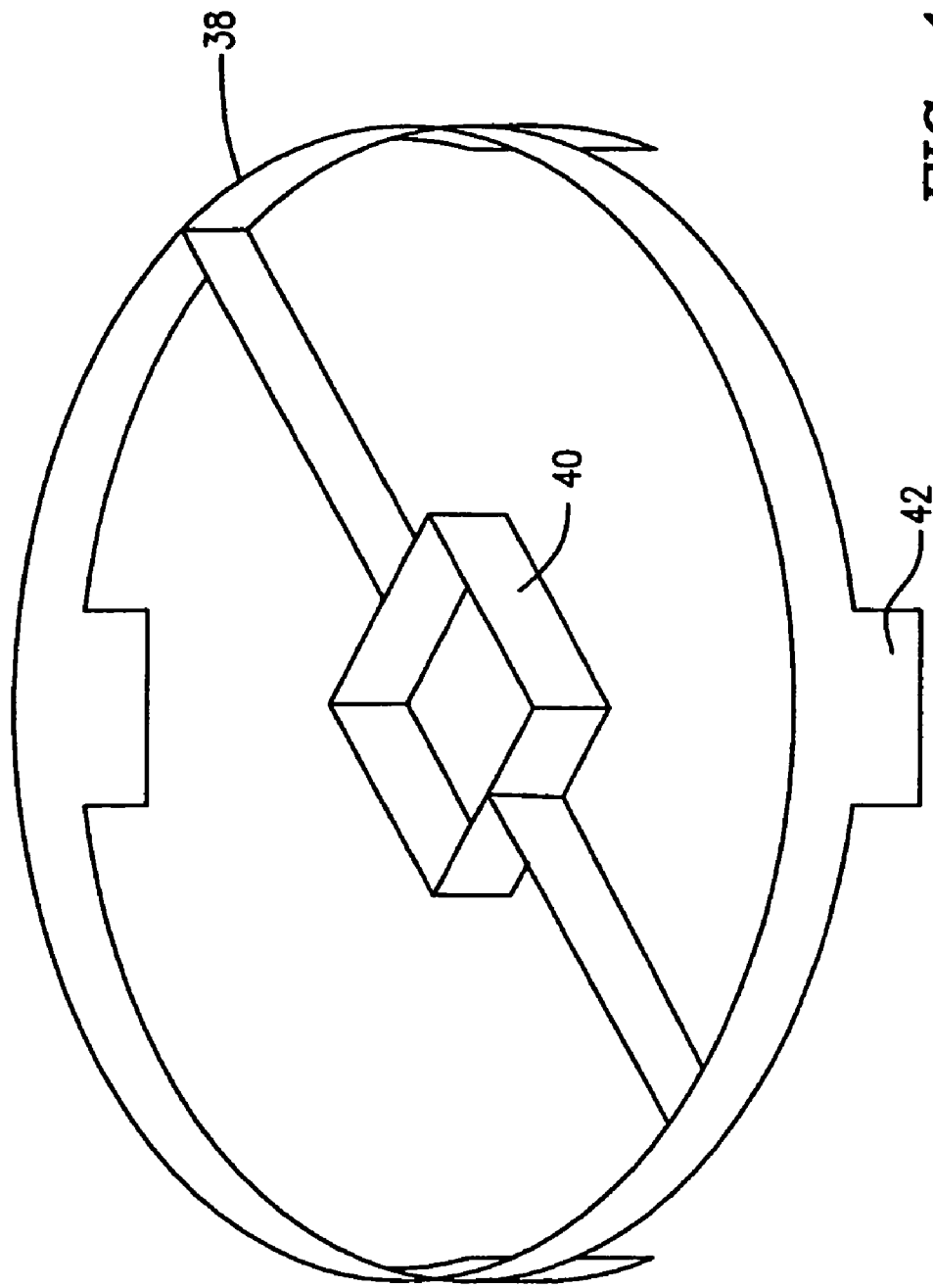
FIG. 13 depicts a secondary holder of the present invention.

In addition, the present invention may be adapted for use with other apparatus including, but not limited to, such as or similar to that described in USP 25 <711> Dissolution including, but not limited to, that known as the "type 2" or "paddle" apparatus. FIG. 13 depicts a secondary holder 38 that may be useful in the practice of such an embodiment comprised of a base 42 and an engaging means 40. In this embodiment, the secondary holder 38 may engage the dosage form holder via the engaging means 40. The secondary holder 38 depicted is circular and is configured so that it may be placed on the bottom interior section of a conventional dissolution vessel without requiring the modification of commercially available dissolution equipment. In other embodiments, the secondary holder may be of any shape and/or size known to those skilled in the art. In certain embodiments, the holder may be engaged with the secondary holder by use of an engaging means that is magnetic. However, other engaging means known to those skilled in the art are also within the full-intended scope of the present invention.

The secondary holder 38 may be configured as a separate or a unitary member integral with the holder 10 (not shown). The secondary holder 38 is preferably fabricated of stainless steel, plastic or other material (or any combination thereof) that is not easily corrodible by the dissolution medium, which may be acidic. The secondary holder 38 may also be fabricated of materials such that it will have a density greater than that of the dissolution mediums used so that it will rest on the bottom of the testing vessel to be used. However, the secondary holder 38 may be constructed of any suitable materials known to those skilled in the art.

Figure 14:
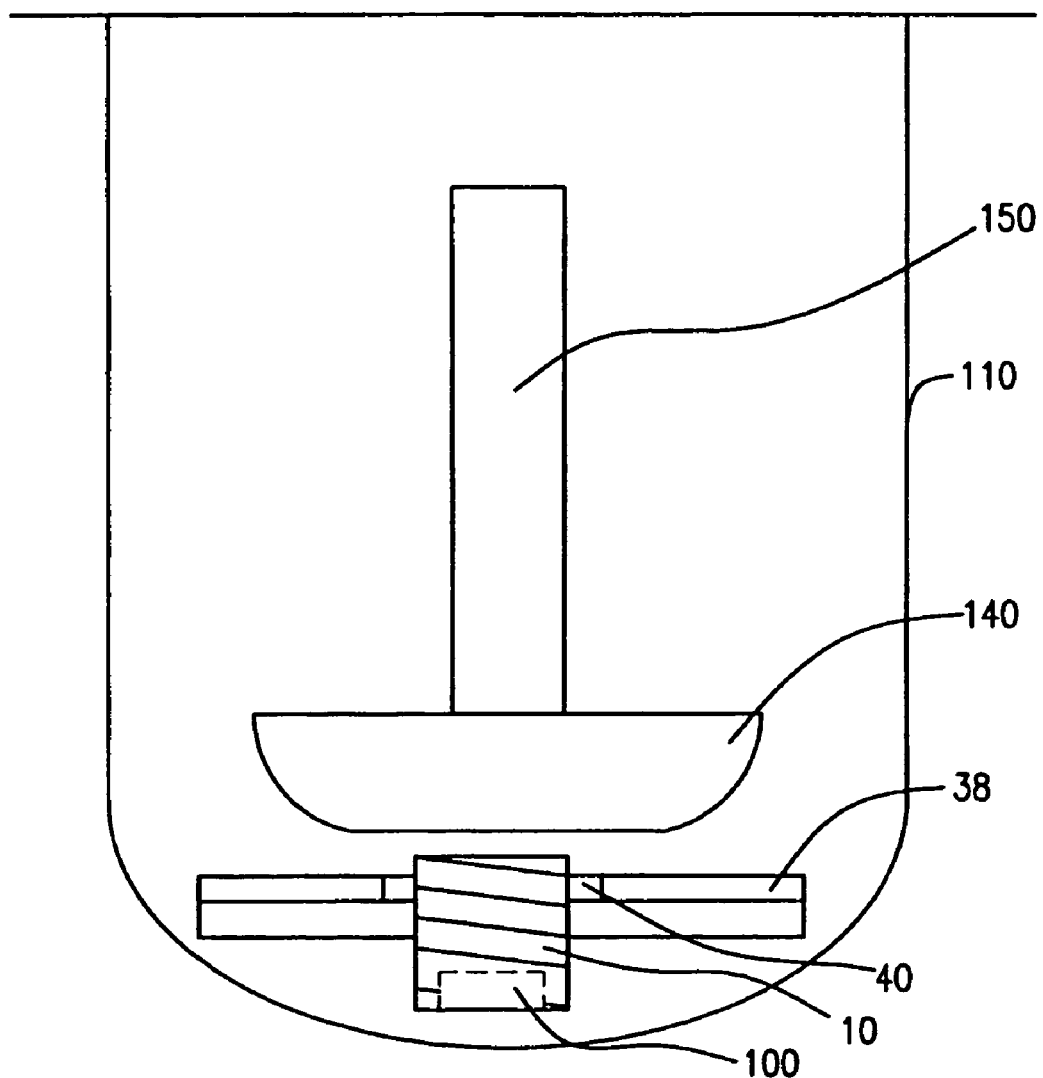
FIG. 14 depicts the embodiment of the present invention shown in FIG. 1 as it is used in a USP 25 <711> Dissolution type 2 apparatus with the secondary holder shown in FIG. 13.
Figure 15:
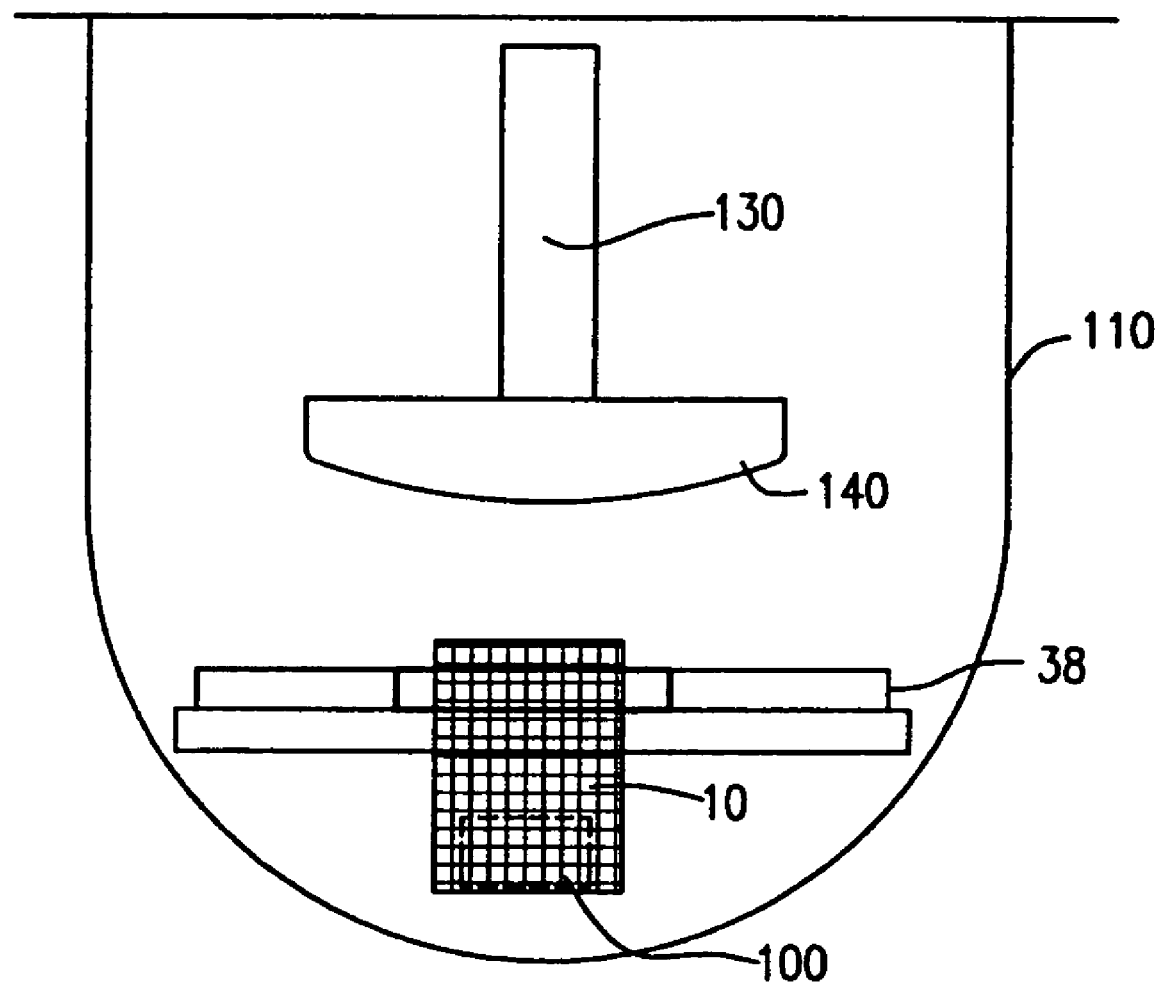
FIG. 15 depicts the embodiment of the present invention shown in FIG. 9 as it is used in a USP 25 <711> Dissolution type 2 apparatus with the secondary holder shown in FIG. 13.

Referring now to FIG. 14 and FIG. 15, it is shown that the secondary holder 38 centers the holder 10 for the dosage form such as a tablet 100 in the vessel 110 and maintains the position of the holder 10 throughout testing using a USP paddle (formed by a blade 140 and shaft 150) or the like. Although in this embodiment the dosage form 100 is held in the center of the bottom of the vessel 110, if it is desired to test the dosage form in an "off center" or other position, the secondary holder may be configured and/or designed accordingly.

Figure 16:
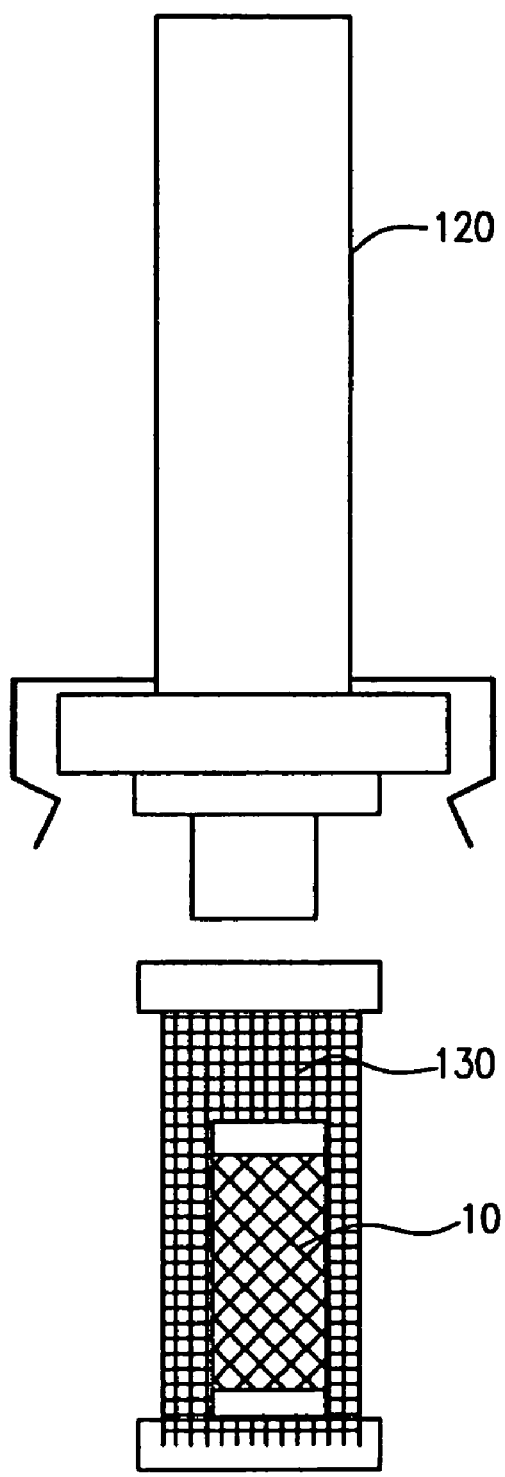
FIG. 16 depicts an embodiment of the present invention wherein the holder is attached to a USP 25 <711> Dissolution type 1 apparatus dissolution basket.
Figure 17:
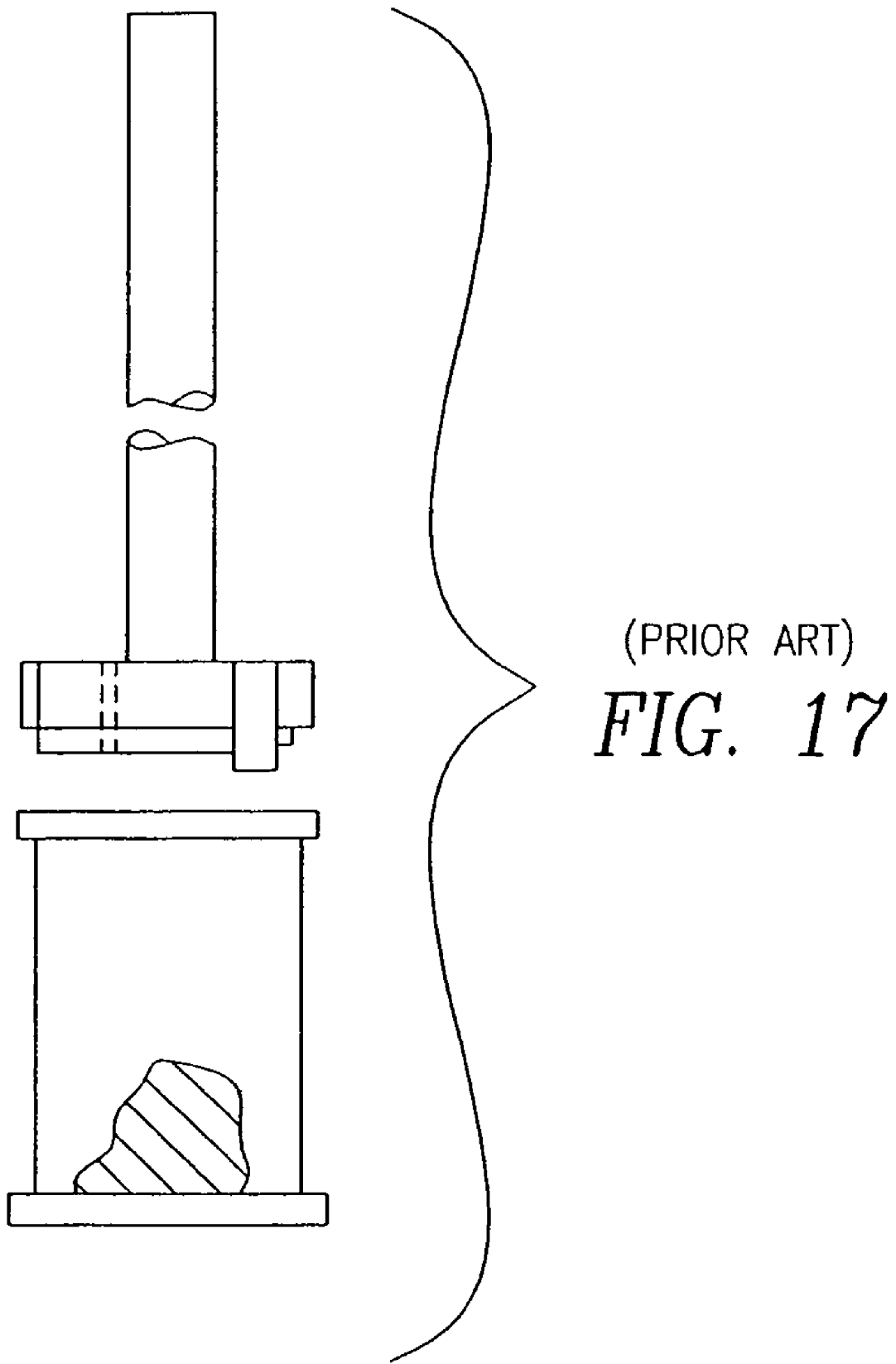
FIG. 17 depicts the basket stirring element of USP 25 <711> Dissolution Type 1 Apparatus.
Figure 18:
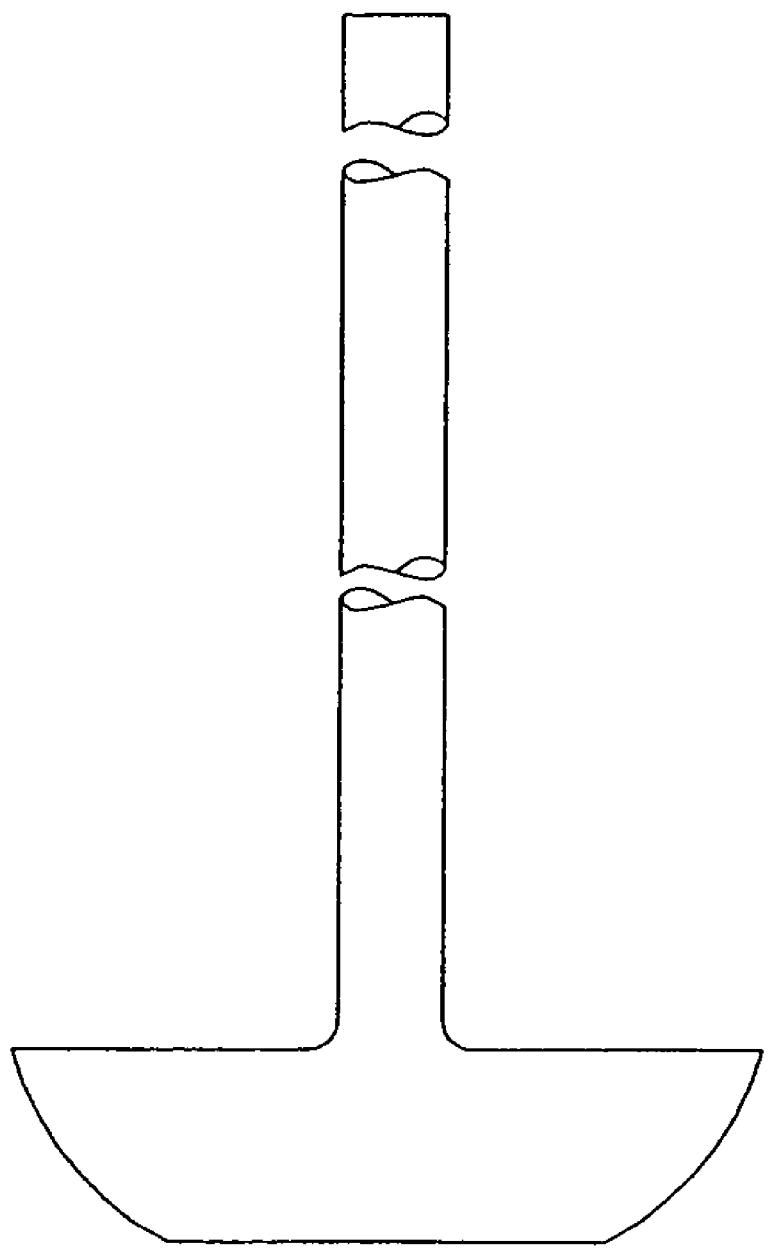
FIG. 18 depicts the paddle stirring element of USP 25 <711> Dissolution Type 2 Apparatus.
Figure 19:
FIG. 19 depicts the oral extended-release tablet holder of USP 25 <724> Drug Release Apparatus 7.

FIG. 16 depicts one example of an embodiment of the present invention wherein the holder 10 inside the dissolution basket 130 and the dissolution basket is attached to the rotating shaft 120. In such embodiments, the holder may be removably attached and/or permanently attached to the basket.

All of the above referenced patents are incorporated herein by reference. While this invention has been described with reference to specific embodiments thereof, it is not limited thereto. Instead, the claims which follow are intended to be construed to encompass not only the forms and embodiments of the invention shown and described, but also such other forms and embodiments and such variants and modifications thereof as may be devised by those skilled in the art without departing from the spirit and scope of the present invention as may be ascertained from the foregoing description and accompanying drawings.

The invention claimed is:

1. A method of performing immersion testing comprising the steps of:
    placing a dosage form in a device that holds the dosage form in a specific orientation;
    placing said device and the dosage form in an apparatus for immersion testing; and
    conducting immersion testing wherein the apparatus for immersion testing is a USP 25 <711> Dissolution Type 1 Apparatus.

2. The method of claim 1 wherein the step of placing the dosage form in said device comprises horizontally orienting a dosage form in said device.

3. The method of claim 1 wherein the step of placing the dosage form in said device comprises vertically orienting a dosage form in said device.

4. The method of claim 1 wherein the dosage form is a matrix tablet.

5. The method of claim 1 wherein the dosage form is a tablet.

6. The method of claim 1 wherein the dosage form is an osmotic tablet with at least one passageway.

7. The method of claim 6 wherein the device orients the tablet such that a passageway of the tablet faces in the upward direction.

8. The method of claim 6 wherein the device orients the tablet such that a passageway of the tablet faces in the downward direction.

9. The method of claim 6 wherein the device orients the tablet such that a passageway of the tablet faces to a side.

10. A method of performing immersion testing comprising the steps of:

placing a dosage form in a device that holds the dosage form in a specific orientation;

attaching the device to a secondary holding means;

placing the secondary holding means with the attached device and the dosage form in a vessel for conducting immersion testing; and conducting immersion testing; wherein the secondary holding means is a basket in a USP 25 <711> Dissolution Type I Apparatus.

11. The method of claim 10 wherein the dosage form is a tablet.

* * * * *